United States Patent [19]

Essex et al.

[11] Patent Number: 6,103,238
[45] Date of Patent: Aug. 15, 2000

[54] SELECTIVELY DEGLYCOSYLATED HUMAN IMMUNODEFICIENCY VIRUS TYPE 1 ENVELOPE VACCINES

[75] Inventors: Myron E. Essex, Sharon; Tun-Hou Lee, Newton; Woan-Ruoh Lee; Chun-Nan Lee, both of Brookline, all of Mass.

[73] Assignee: President and Fellows of Harvard College, Cambridge, Mass.

[21] Appl. No.: 07/850,770

[22] Filed: Mar. 13, 1992

[51] Int. Cl.[7] .......................... A61K 39/21; A61K 39/395; A61K 39/42; A61K 39/40

[52] U.S. Cl. ................................. 424/188.1; 424/130.1; 424/139.1; 424/208.1; 424/141.1; 424/142.1; 424/147.1; 424/148.1; 530/395; 530/387.5; 530/387.9; 530/388.35

[58] Field of Search .................................... 424/89, 130.1, 424/188.1, 133.1, 208.1, 141.1, 142.1, 147.1, 148.1; 530/395, 387, 398, 388.1, 387.1, 387.9, 388.38

[56] References Cited

PUBLICATIONS

Bolmstedt, et al, J of Gen Virology, 72:1269–1277, 1991.
Woan–Ruoh, et al, Final Program and Abstracts, 6th International Conference on Aids, San Francisco, CA 3:S.A.8, 1990.
Feizi, et al, Glycobiology 1:17–23, 1990.
Cohen, et al, J of Acquired Immune Deficiency Syndromes, 3:11–18, 1990.
Syu, et al, PNAS, 87:3695–3699, 1990.
Aldovini, et al, J of Virology, 64:1920–1926, 1990.
Leonard, et al, The J of Biol Chem, 265:10373–10382, 1990.
Kozarsky, et al, J of Acquired Immune Deficiency Syndromes, 2:163–169, 1989.
Cohen, et al, Nature, 334:532–534, 1988.
Willey, et al, J of Virology, 62:139–147, 1988.
Chou, et al, The J of Infectious Disease, 157:805–811, 1988.
Geyer, et al, The J of Bio Chem, 263:11760–11767, 1988.
Curran, et al, Science, 239:610–616, 1988.
Mizuochi, et al, Biochem J, 254:599–603, 1988.
Lasky, et al, Cell, 50:975–985, 1987.
Matthews, et al, PNAS, 84:5424–5428, 1987.
Pyle, et al, Aids Research and Human Retroviruses, 3:387–400, 1987.
Lasky, et al, Science, 233:209–212, 1986.
McDougal, et al, Science, 231:382–385, 1986.
Cullen, et al, Cell, 46:973–982, 1986.

Robey, et al, PNAS, 83:7023–7027, 1986.
Veronese, et al, Science, 229:1402–1404, 1985.
Robey, et al, Science, 228:593–595, 1985.
Klatzmann, et al, Nature, 321:767–768, 1984.
Dalgleish, et al, Nature, 312:763–767, 1984.
Allan, et al, Science 228:1091–1094, 1985.
Botarelli et al., "N–glycosylation of HIV–gp120 may constrain recognition by T lymphocytes", J. Immunol., 147(9):3128–32 (1991).
Lee et al., "Non–random Distribution of GP 120 N–linked Glycosylation Sites Critical for HIV–1 Infectivity", AIDS Research and Human Retroviruses, 8(5):917 (1992).
Lee et al., "Nonrandom distribution of gp120 N–linked Glycosylation Sites Important for Infectivity of Human Immunodeficiency Virus Type 1", PNAS USA, 89(6):2213–17 (1992).
Dirckx et al.; Mutation of conserved n–glycosylation . . . ; Vir. Res.; vol. 18(1); pp. 9–20, Dec. 1990.
Bolmstedt et al.; Effects of mutations in glycosylation sites . . . ; J. Gen. Vir.; vol. 72; pp. 1269–1277, Jun. 1991.
Lee, et al, 1990, "Role of N–linked Oligosaccharides of HIV–1 . . . " Abstract No. S.A.8, 6th International Conference on AIDS, Jun. 24, 1990.
Davis, et al., 1990, "Glycosylation Governs the Binding of . . . " J. of General Virology 71:2889–2898.

*Primary Examiner*—Jeffrey Stucker
*Assistant Examiner*—Bret Nelson
*Attorney, Agent, or Firm*—Fish & Richardson, P.C.

[57] ABSTRACT

Selective deglycosylation of HIV-1 envelope proteins enhances their ability to elicit a protective immune response in people. Glycosylation can reduce or prevent immunological recognition of envelope protein domains. Selective deglycosylation exposes these domains and improves the opportunity for a protective immune response. Deglycosylation which produces substantial conformational changes (as determined by loss of infectivity) should be avoided. Recombinant HIV-1 envelope glycoproteins are generated which have primary amino acid sequence mutation(s) in consensus sequence(s) for N-linked glycosylation (sugar attachment), so as to prevent glycosylation at that site(s). The position of such genetic deglycosylation is important and should be between the C terminus of gp120 and the Cys at the N-terminal side of the cysteine loop containing the hyper-variable region 3 (V3) (this Cys is generally positioned about at residue 296, counting from the N-terminus of gp120). The mutant glycoprotein should be deglycosylated such that the total molecular mass of the mutant gp120 component is less than 90% (more preferably less than 75%) of the corresponding fully glycosylated wild type gp120 component to maximize a useful immune response.

10 Claims, 6 Drawing Sheets

SEQUENCE LISTING

```
(1) GENERAL INFORMATION:

(iii) NUMBER OF SEQUENCES:    30

(2) INFORMATION FOR SEQ ID NO:    1:

(i) SEQUENCE CHARACTERISTICS:
          (A) LENGTH:               28
          (B) TYPE:                 nucleic acid
          (C) STRANDEDNESS:         single
          (D) TOPOLOGY:             linear (xi) SEQUENCE DESCRIPTION: SEQ ID NO: 1:

TAGTATTGGT ACAGGTGACA GAAAATTT                                          28

(2) INFORMATION FOR SEQ ID NO:    2:

(i) SEQUENCE CHARACTERISTICS:
          (A) LENGTH:               24
          (B) TYPE:                 nucleic acid
          (C) STRANDEDNESS:         single
          (D) TOPOLOGY:             linear (xi) SEQUENCE DESCRIPTION: SEQ ID NO: 2:

TGATTTGAAG CAGGATACTA ATAC                                              24

(2) INFORMATION FOR SEQ ID NO:    3:

(i) SEQUENCE CHARACTERISTICS:
```

```
            (A) LENGTH:              27
            (B) TYPE:                nucleic acid
            (C) STRANDEDNESS:        single
            (D) TOPOLOGY:            linear (xi) SEQUENCE DESCRIPTION: SEQ ID NO: 3:

ATACTAATAC CCAAAGTAGT AGCGGGA                                           27

(2) INFORMATION FOR SEQ ID NO:    4:

(i) SEQUENCE CHARACTERISTICS:
            (A) LENGTH:              23
            (B) TYPE:                nucleic acid
            (C) STRANDEDNESS:        single
            (D) TOPOLOGY:            linear (xi) SEQUENCE DESCRIPTION: SEQ ID NO: 4:

GATAAACAGT GCTCTTTCAA TAT                                               23

(2) INFORMATION FOR SEQ ID NO:    5:

(i) SEQUENCE CHARACTERISTICS:
            (A) LENGTH:              24
            (B) TYPE:                nucleic acid
            (C) STRANDEDNESS:        single
            (D) TOPOLOGY:            linear (xi) SEQUENCE DESCRIPTION: SEQ ID NO: 5:

CTGCTCTTTC CAGATCAGCA CAAG                                              24

(2) INFORMATION FOR SEQ ID NO:    6:

(i) SEQUENCE CHARACTERISTICS:
            (A) LENGTH:              26
            (B) TYPE:                nucleic acid
            (C) STRANDEDNESS:        single
            (D) TOPOLOGY:            linear (xi) SEQUENCE DESCRIPTION: SEQ ID NO: 6:

TACCAATAGA TCAGGATACT ACCAGC                                            26

(2) INFORMATION FOR SEQ ID NO:    7:

(i) SEQUENCE CHARACTERISTICS:
            (A) LENGTH:              25
            (B) TYPE:                nucleic acid
            (C) STRANDEDNESS:        single
            (D) TOPOLOGY:            linear (xi) SEQUENCE DESCRIPTION: SEQ ID NO: 7:

TGACAAGTTG TCAGACCTCA GTCAT                                             25

(2) INFORMATION FOR SEQ ID NO:    8:

(i) SEQUENCE CHARACTERISTICS:
            (A) LENGTH:              24
            (B) TYPE:                nucleic acid
            (C) STRANDEDNESS:        single
            (D) TOPOLOGY:            linear (xi) SEQUENCE DESCRIPTION: SEQ ID NO: 8:

TAAAATGTAA TCATAAGACG TTCA                                              24

(2) INFORMATION FOR SEQ ID NO:    9:

(i) SEQUENCE CHARACTERISTICS:
            (A) LENGTH:              26
```

```
            (B) TYPE:                nucleic acid
            (C) STRANDEDNESS:        single
            (D) TOPOLOGY:            linear (xi) SEQUENCE DESCRIPTION: SEQ ID NO: 9:

ATAAGACGTT CCATGGAACA GGACCA                                           26

(2) INFORMATION FOR SEQ ID NO:    10:

(i) SEQUENCE CHARACTERISTICS:
            (A) LENGTH:              27
            (B) TYPE:                nucleic acid
            (C) STRANDEDNESS:        single
            (D) TOPOLOGY:            linear (xi) SEQUENCE DESCRIPTION: SEQ ID NO: 10:

GACCATGTAC ACAGGTCAGC ACAGTAC                                          27

(2) INFORMATION FOR SEQ ID NO:    11:

(i) SEQUENCE CHARACTERISTICS:
            (A) LENGTH:              23
            (B) TYPE:                nucleic acid
            (C) STRANDEDNESS:        single
            (D) TOPOLOGY:            linear (xi) SEQUENCE DESCRIPTION: SEQ ID NO: 11:

ACTGCTGTTA CAAGGCAGTC TAG                                              23

(2) INFORMATION FOR SEQ ID NO:    12:

(i) SEQUENCE CHARACTERISTICS:
            (A) LENGTH:              26
            (B) TYPE:                nucleic acid
            (C) STRANDEDNESS:        single
            (D) TOPOLOGY:            linear (xi) SEQUENCE DESCRIPTION: SEQ ID NO: 12:

TTAGATCTGT CCAGTTCACG GACAAT                                           26

(2) INFORMATION FOR SEQ ID NO:    13:

(i) SEQUENCE CHARACTERISTICS:
            (A) LENGTH:              27
            (B) TYPE:                nucleic acid
            (C) STRANDEDNESS:        single
            (D) TOPOLOGY:            linear (xi) SEQUENCE DESCRIPTION: SEQ ID NO: 13:

TAGTACAGCT GCAGACATCT GTAGAAA                                          27

(2) INFORMATION FOR SEQ ID NO:    14:

(i) SEQUENCE CHARACTERISTICS:
            (A) LENGTH:              24
            (B) TYPE:                nucleic acid
            (C) STRANDEDNESS:        single
            (D) TOPOLOGY:            linear (xi) SEQUENCE DESCRIPTION: SEQ ID NO: 14:

CTGTAGAAAT TCAATGTACA AGAC                                             24

(2) INFORMATION FOR SEQ ID NO:    15:

(i) SEQUENCE CHARACTERISTICS:
            (A) LENGTH:              26
            (B) TYPE:                nucleic acid
```

```
            (C) STRANDEDNESS:        single
            (D) TOPOLOGY:            linear (xi) SEQUENCE DESCRIPTION: SEQ ID NO: 15:

ACAAGACCCA ACCACAATAC AAGAAA                                              26

(2) INFORMATION FOR SEQ ID NO:    16:

(i) SEQUENCE CHARACTERISTICS:
            (A) LENGTH:              23
            (B) TYPE:                nucleic acid
            (C) STRANDEDNESS:        single
            (D) TOPOLOGY:            linear (xi) SEQUENCE DESCRIPTION: SEQ ID NO: 16:

GCACATTGTC ACATTAGTAG AGC                                                 23

(2) INFORMATION FOR SEQ ID NO:    17:

(i) SEQUENCE CHARACTERISTICS:
            (A) LENGTH:              25
            (B) TYPE:                nucleic acid
            (C) STRANDEDNESS:        single
            (D) TOPOLOGY:            linear (xi) SEQUENCE DESCRIPTION: SEQ ID NO: 17:

GCAAAATGGC AGAACACTTT AAAAC                                               25

(2) INFORMATION FOR SEQ ID NO:    18:

(i) SEQUENCE CHARACTERISTICS:
            (A) LENGTH:              29
            (B) TYPE:                nucleic acid
            (C) STRANDEDNESS:        single
            (D) TOPOLOGY:            linear (xi) SEQUENCE DESCRIPTION: SEQ ID NO: 18:

ATTCGGAAAT CAGAAAACAA TAATCTTTA                                           29

(2) INFORMATION FOR SEQ ID NO:    19:

(i) SEQUENCE CHARACTERISTICS:
            (A) LENGTH:              25
            (B) TYPE:                nucleic acid
            (C) STRANDEDNESS:        single
            (D) TOPOLOGY:            linear (xi) SEQUENCE DESCRIPTION: SEQ ID NO: 19:

TTTCTACTGT CAGTCAACAC AACTG                                               25

(2) INFORMATION FOR SEQ ID NO:    20:

(i) SEQUENCE CHARACTERISTICS:
            (A) LENGTH:              30
            (B) TYPE:                nucleic acid
            (C) STRANDEDNESS:        single
            (D) TOPOLOGY:            linear (xi) SEQUENCE DESCRIPTION: SEQ ID NO: 20:

ACAACTGTTT CAGAGTACTT GGTTTAATAG                                          30

(2) INFORMATION FOR SEQ ID NO:    21:

(i) SEQUENCE CHARACTERISTICS:
            (A) LENGTH:              25
            (B) TYPE:                nucleic acid
            (C) STRANDEDNESS:        single
```

```
            (D) TOPOLOGY:          linear (xi) SEQUENCE DESCRIPTION: SEQ ID NO: 21:

GTACTTGGTT TCAGAGTACT TGGAG                                         25

(2) INFORMATION FOR SEQ ID NO:   22:

(i) SEQUENCE CHARACTERISTICS:
            (A) LENGTH:            26
            (B) TYPE:              nucleic acid
            (C) STRANDEDNESS:      single
            (D) TOPOLOGY:          linear (xi) SEQUENCE DESCRIPTION: SEQ ID NO: 22:

CTGAAGGGTC ACATAACACT GAAGGA                                        26

(2) INFORMATION FOR SEQ ID NO:   23:

(i) SEQUENCE CHARACTERISTICS:
            (A) LENGTH:            26
            (B) TYPE:              nucleic acid
            (C) STRANDEDNESS:      single
            (D) TOPOLOGY:          linear (xi) SEQUENCE DESCRIPTION: SEQ ID NO: 23:

GATGTTCATC ACAGATTACA GGGCTG                                        26

(2) INFORMATION FOR SEQ ID NO:   24:

(i) SEQUENCE CHARACTERISTICS:
            (A) LENGTH:            26
            (B) TYPE:              nucleic acid
            (C) STRANDEDNESS:      single
            (D) TOPOLOGY:          linear (xi) SEQUENCE DESCRIPTION: SEQ ID NO: 24:

GGTAATAGCA ACCATGAGTC CGAGAT                                        26

(2) INFORMATION FOR SEQ ID NO:   25:

(i) SEQUENCE CHARACTERISTICS:
            (A) LENGTH:            30
            (B) TYPE:              nucleic acid
            (C) STRANDEDNESS:      single
            (D) TOPOLOGY:          linear (xi) SEQUENCE DESCRIPTION: SEQ ID NO: 25:

GGTAAATGTG GTCGACAACT TTTGACATGT                                    30

(2) INFORMATION FOR SEQ ID NO:   26:

(i) SEQUENCE CHARACTERISTICS:
            (A) LENGTH:            28
            (B) TYPE:              nucleic acid
            (C) STRANDEDNESS:      single
            (D) TOPOLOGY:          linear (xi) SEQUENCE DESCRIPTION: SEQ ID NO: 26:

AATACCAATA GTGCATGCGG GAGAATGG                                      28

(2) INFORMATION FOR SEQ ID NO:   27:

(i) SEQUENCE CHARACTERISTICS:
            (A) LENGTH:            30
            (B) TYPE:              nucleic acid
            (C) STRANDEDNESS:      single
            (D) TOPOLOGY:          linear
```

-continued

```
        (xi) SEQUENCE DESCRIPTION: SEQ ID NO: 27:

CTGCTCTTTC AATATTGCCA CAAGCATAAG                                    30

(2) INFORMATION FOR SEQ ID NO:    28:

(i) SEQUENCE CHARACTERISTICS:
              (A) LENGTH:          26
              (B) TYPE:            nucleic acid
              (C) STRANDEDNESS:    single
              (D) TOPOLOGY:        linear (xi) SEQUENCE DESCRIPTION: SEQ ID NO: 28:

GTTGTAACAC CGAAGTCATT ACACAG                                        26

(2) INFORMATION FOR SEQ ID NO:    29:

(i) SEQUENCE CHARACTERISTICS:
              (A) LENGTH:          33
              (B) TYPE:            nucleic acid
              (C) STRANDEDNESS:    single
              (D) TOPOLOGY:        linear (xi) SEQUENCE DESCRIPTION: SEQ ID NO: 29:

CTGCTGTTAA ATGGCGCTCT AGCAGAAGAA GAG                                33

(2) INFORMATION FOR SEQ ID NO:    30:

(i) SEQUENCE CHARACTERISTICS:
              (A) LENGTH:          29
              (B) TYPE:            nucleic acid
              (C) STRANDEDNESS:    single
              (D) TOPOLOGY:        linear (xi) SEQUENCE DESCRIPTION: SEQ ID NO: 30:

CTGTCAATTT CGTCGTCGAC AATGCTAAA                                     29
```

SELECTIVELY DEGLYCOSYLATED HUMAN IMMUNODEFICIENCY VIRUS TYPE 1 ENVELOPE VACCINES

The invention was supported by the U.S. Government which has certain rights in the invention.

BACKGROUND OF THE INVENTION

The field of the invention is human immunodeficiency virus vaccines and immunotherapeutics.

Human immunodeficiency virus is the etiological agent of acquired immune deficiency syndrome (AIDS). The env gene of HIV encodes a 160 kD glycoprotein that is subsequently cleaved into two smaller species, an extracellular (or surface) protein gp120 and a transmembrane protein gp41 (Allan et al., 1985, Science 228:1091; Di'Marzo-Veronese et al., 1985, Science 229:1402). Gp120 is noncovalently linked to gp41 (Allan et al., 1985, Science 228:1091; Chou et al., 1988, J. Infect. Dis. 157:805; Di'Marzo-Veronese et al., 1985, Science 229:1402; Lasky et al., 1987, Cell 50:975).

Among the various HIV isolates, some sequences are highly conserved and some are variable. Two characteristics of the env glycoprotein are conservation of cysteine residues and of a relatively large number of N-linked carbohydrate sites in HIV-1 isolates. Similar secondary and tertiary structures for the env glycoprotein have been suggested based on the similarity of the sequences of HIV.

The env glycoprotein is heavily glycosylated. The unmodified polypeptide backbone of gp120 (about 480 amino acids) weighs about 55 kD. About one half of the molecular weight of gp120 can be accounted for by attached carbohydrates (Allan et al., 1985, Science 228:1091; Geyer et al., 1988, J. Biol. Chem. 263:11760; Matthews et al., 1987, Proc. Natl. Acad. Sci. USA 84:5424; Mizuochi et al., 1988, Biochem J. 254:599; Robey et al., 1985, Science 228:593). Although gp41 is also a glycoprotein, it is not as heavily glycosylated as gp120 (Di'Marzo-Veronese et al., 1985, Science 229:1402). The oligosaccharides of the gp120/41 complex are generally N-linked with no detectable O-linked sugar residues present (Kozarsky et al., 1989, J. AIDS 2:163; Leonard et al., 1990, J. Biol. Chem. 265:10373). The consensus sequence of the site for N-linked carbohydrate attachment is Asn-X-Ser/Thr, where X is any amino acid except Pro and Asp. HIV-1 molecular clones contain an average of 23–24 potential N-linked carbohydrate attachment sites on gp120 and about 4–7 on gp41. The consensus sites on gp120 are generally glycosylated when the env protein is expressed in chinese hamster ovary (CHO) cells (Leonard et al., 1990, J. Biol. Chem. 265:10373).

CD4 is the host cell receptor for HIV (Dalgleish et al., 1984, Nature 312:763; Klatzmann et al., 1984, Nature 312:767; McDougal et al., 1986, Science 231:382). The CD4-binding domain of HIV has been mapped to the C-terminal region of gp120 (Kowalski et al., 1987, Science 231:1351; Lasky et al., 1987, Cell 50:975), although it is reported that sequences in the N-terminal region of gp120 may also be involved (Syu et al., 1990, Proc. Natl. Acad. Sci. USA 87:3695).

Vaccines and immunotherapeutics comprising native gp120 and gp160 have been proposed.

SUMMARY OF THE INVENTION

We have discovered that selectively deglycosylated HIV-1 envelope proteins retain their ability to support viral infectivity, implying that they generally retain the native envelope conformation. We also noted that the envelope protein of the related simian virus for African green monkeys ($SIV_{AGM}$), which is not pathogenic to its natural host, has fewer N-linked glycosylation sites, particularly in the C-terminal portion of the surface envelope protein analogous to gp120. Without wishing to bind ourselves to a specific detailed molecular explanation, we propose that a selectively deglycosylated HIV-1 envelope protein is more effective in eliciting a protective immune response in people. Glycosylation serves to reduce or prevent immunological recognition of envelope protein domains. Selective deglycosylation enables an immune response to these domains and improves the opportunity for a protective immune response. Deglycosylation which produces substantial conformational changes (as determined by loss of infectivity) should be avoided.

We have further found that the invention can be achieved by generating recombinant HIV-1 envelope glycoproteins which have primary amino acid sequence mutation(s) in consensus sequence(s) for N-linked glycosylation (sugar attachment), so as to prevent glycosylation at that site(s). Moreover, we have found that the position of such genetic deglycosylation is important. Preferably, the position of such genetic deglycosylation should be between the C terminus of gp120 and the Cys at the N-terminal side of the cysteine loop containing the hypervariable region 3 (V3) (this Cys is generally positioned about at residue 296, counting from the N-terminus of gp120). We have found that it is important to remove at least a minimum amount of the total native gp120 carbohydrate in order to maximize the opportunity for a useful immune response. Specifically, the mutant glycoprotein should be deglycosylated such that the total molecular mass of the mutant gp120 component is less than 90% (more preferably 75%) of the corresponding fully glycosylated wild type gp120 component.

Another indicia of a suitable conformation for a desirable immune response is infectivity—i.e., the mutant glycoprotein (when present as a component of a complete HIV-1 virion) enables viral infectivity. By retaining viral infectivity, we mean that when the envelope gene of HIV or an infectious DNA clone is engineered to encode the mutations of the mutant envelope glycoprotein, the virus retains infectivity.

By wild-type or native HIV-1 envelope glycoprotein we mean the envelope glycoprotein encoded by a naturally occurring HIV-1 isolate. With respect to designation of amino acid positions of the envelope glycoprotein such as the Cys at the N-terminal side of the cyteine loop containing V3 (approximately amino acid position 296), it will be understood that certain aspects of envelope structure are conserved throughout virtually all HIV-1 strains, and those conserved structures can be used as landmarks. For example cysteine cross-links form loops which contain hypervariable regions having widely accepted designations.

By the term "recombinant glycoprotein" we mean a glycoprotein produced by expression of a DNA sequence that does not occur in nature and which results from human manipulations of DNA bases. The term envelope glycoprotein means gp160, gp120, or other env-encoded peptides containing at least the above-described C-terminal portion of gp120.

Accordingly, one aspect of the invention features compositions comprising mutant selectively deglycosylated HIV-1 recombinant envelope glycoproteins as described above. Other aspects of the invention feature vaccines (both for protecting uninfected individuals and for treating infected individuals) that comprise such mutant HIV-1 recombinant envelope proteins. Still other aspects of the invention feature DNA encoding the mutant HIV-1 recombinant envelope proteins (particularly in an expression vector), recombinant cells comprising such DNA, and methods of making the recombinant mutant envelope glycoproteins by expressing such DNA. Still another aspect of the invention features antibodies raised, or preferentially binding to, the mutant envelope glycoprotein.

In preferred embodiments, mutants of either gp120 or gp160 can be used. Because the deglycosylation unmasks envelope regions which are generally conserved, it is possible to use any of a wide range of HIV-1 strains or isolates e.g., MN, HXB2, LAI, NL43, MFA, BRVA, SC, JH3, ALAI, BALI, JRCSF, OYI, SF2, NY5CG, SF162, JFL, CDC4, SF33, AN, ADA, WMJ2, RF, ELI, Z2Z6, NDK, JY1, MAL, U455, Z321. The preferred mutation at the consensus N-linked glycosylation sequence is substitution of Asn, Ser or Thr with a different amino acid (i.e., any amino acid other than the one occupying the position in the wild type). Preferably, there are multiple deglycosylations in the above described C-terminal region, particularly in the region between the C terminus of gp120 and the Cys on the N-terminal side of the cysteine loop containing hypervariable region 4 (V4). For example, one or more of the positions 386, 392, 397, 406 or 463 may be deglycosylated. We have found that in some cases the consensus sequence closest to position 448 and/or position 392 may be mutated, together with other C-terminal consensus sequence mutations. We have also found that it is preferable to maintain glycosylation at the consensus sequence closest to position 289. It may also be desirable in some constructions to maintain glycosylation at position 356. For convenience the numbers given above gp120 refer to amino acid residues of the HXB2 envelope protein. Those skilled in the field will understand that conservation of envelope features in other strains will permit the application of the invention to the envelope proteins of those strains. For example, there is conservation of cysteine cross-links that define loops with hypervariable regions. Thus, the reference to positions 386, 392, 397, 406 and 463 can be understood as a reference to the N-linked glycosylation sites positioned between the C-terminus of gp120 and the Cys on the N-terminal side of the cysteine loop containing hypervariable region 4 (V4). Similarly, the reference to positions 289 and 356 can be applied to other strains with reference to FIG. 1 and FIG. 2.

Other features and advantages of the invention will be apparent from the following description of preferred embodiments and from the claims.

DETAILED DESCRIPTION

The drawings are first briefly described.

Drawings

Figure 1:
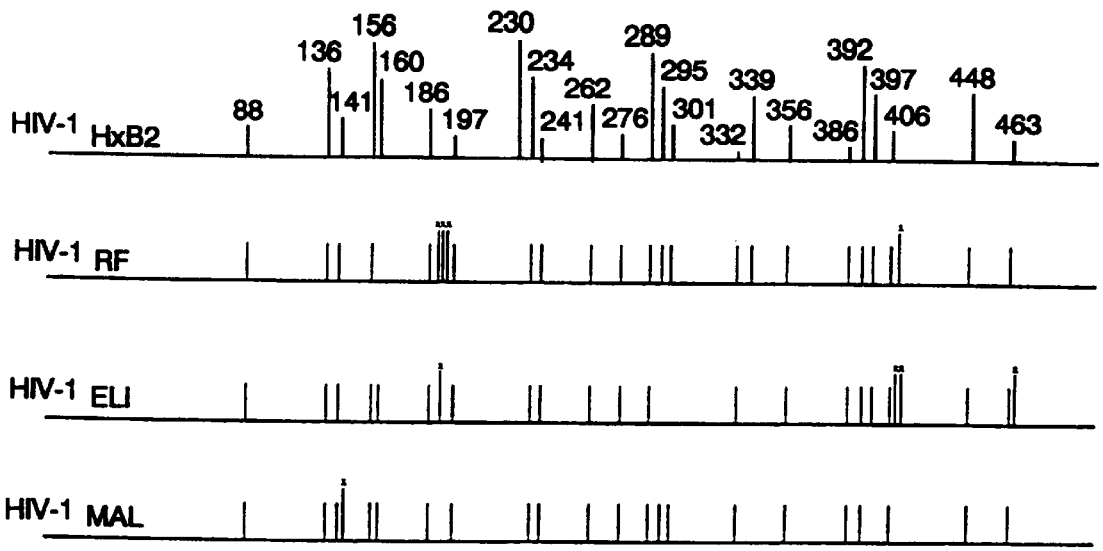

FIG. 1 is a diagram depicting the conservation of N-linked glycosylation sites in gp120 of selected HIV-1 isolates. Twenty-four consensus N-linked glycosylation sites of HXB2 are shown by lines. The numbers above each line indicate the amino acid positions in HXB2. The longer lines with an asterisk symbol represent N-linked glycosylation sites not present in HXB2.

Figure 2:
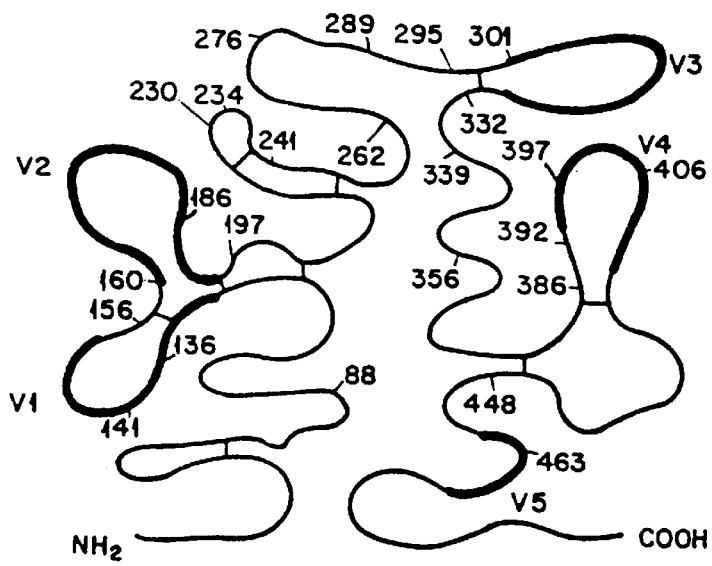

FIG. 2 is a schematic drawing of gp120. Darkened lines represent the hypervariable regions of the molecule which form 5 loops, designated V1–5, via cysteine-cysteine disulfide bonds which are represented by the solid lines connecting each end of a loop. The numbers represent the first amino acid in each of the 24 potential N-linked glycosylation sites in the molecule.

Figure 3:
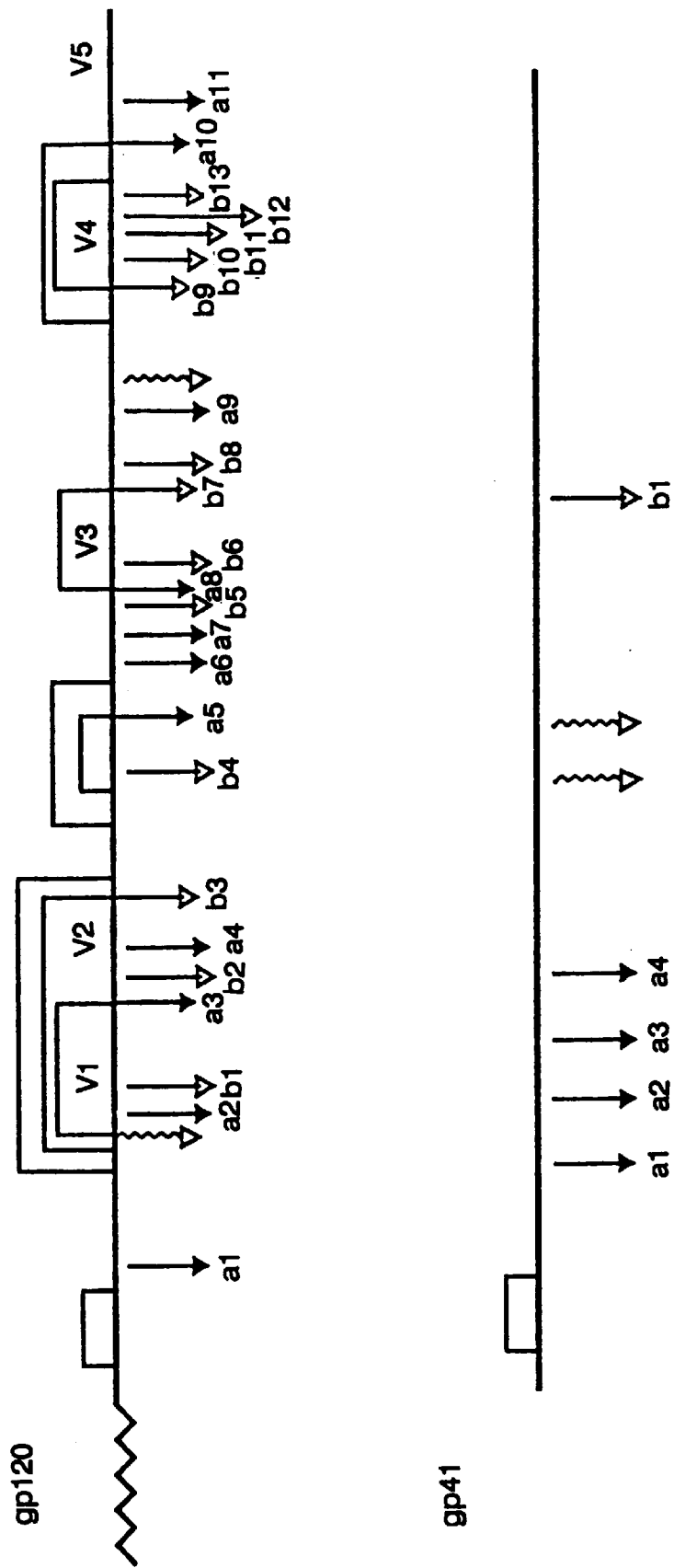

FIG. 3 is a schematic diagram of gp120 from HIV-1. The distribution and amount of conservation of N-linked glycosylation sites is shown. Amino acids are numbered from the N-terminus of the molecule to the C-terminus. The numbers beneath the diagram denote the position of the first amino acid in the consensus sequence of an N-linked glycosylation site. Sites which are $\geq 90\%$ conserved among HIV-1, HIV-2 and SIV isolates are indicated by an arrow with a solid head and are numbered sequentially with the prefix 'a'. Sites which are at least 50% conserved are indicated by an arrow with an open head and are numbered sequentially with the prefix 'b'. Other sites which are conserved at a level of less than 50% are indicated by an arrow with a wavy tail.

Figure 4:
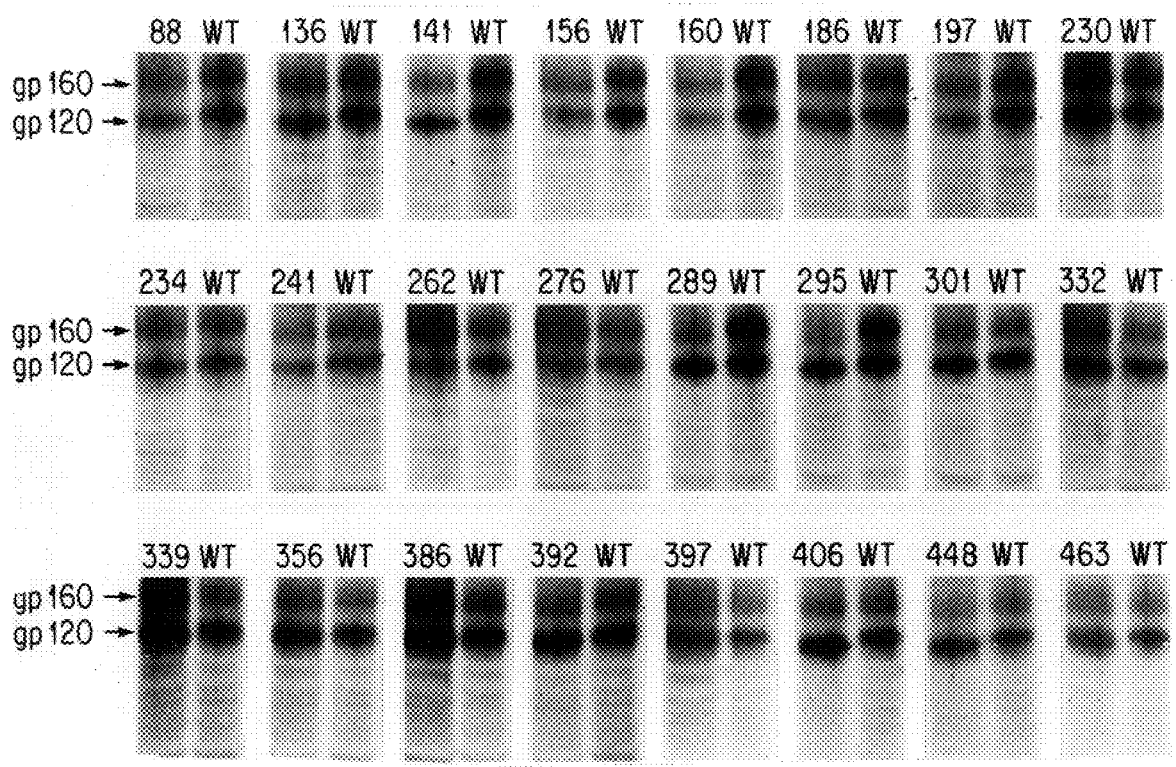

FIG. 4 is a western blot demonstrating expression of gp160 and gp120 in COS-1 cells transfected with wild type or mutant proviral DNA. Cell lysates from transfected COS-1 cells were separated on 12% SDS-polyacrylamide gels, transferred to nitrocellulose filters, and then reacted with a reference sheep anti-gp120 serum. The wild type virus is abbreviated WT and N-linked glycosylation mutants are indicated by numbers representing their position in HXB2.

Figure 5:
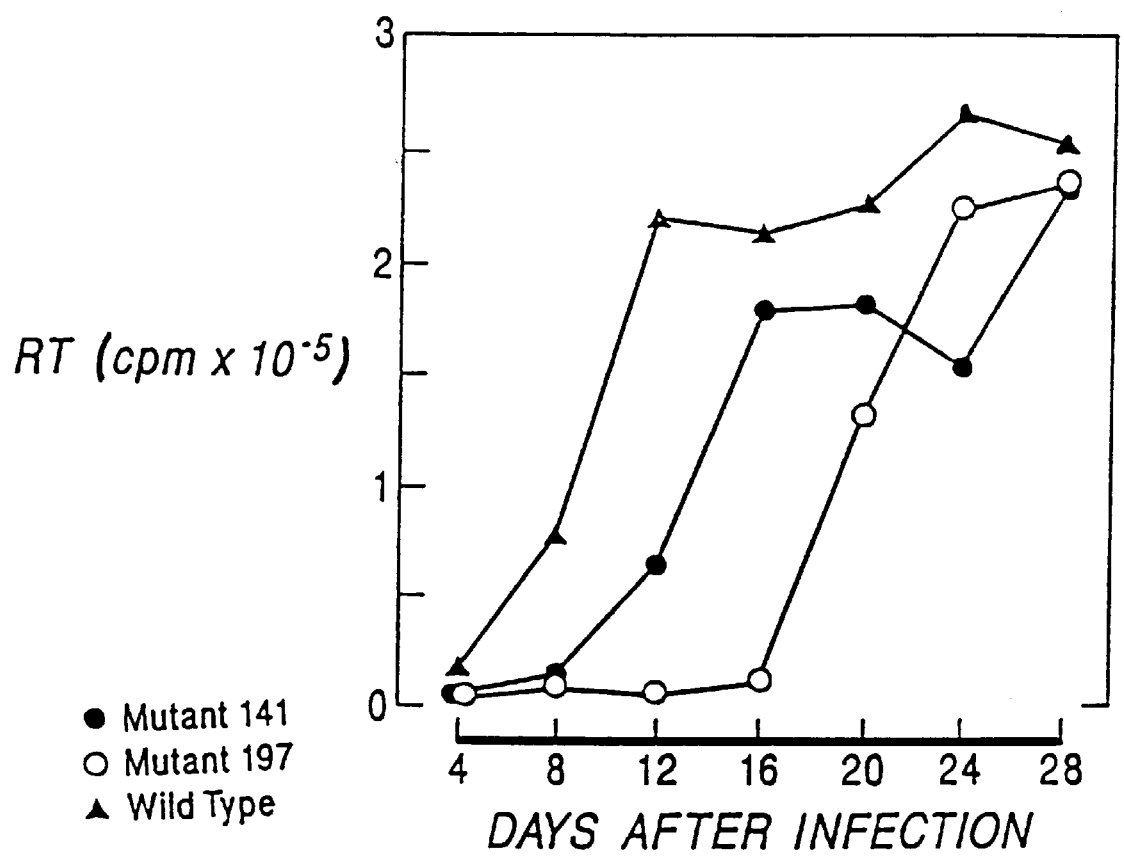

FIG. 5 is a graphical demonstration of infection of CD4-positive SupT1 cells by N-linked glycosylation mutants. Reverse transcriptase activity in cultured supernatants of SupT1 cells infected by wild type (WT) virus and by mutant viruses 141 or 197, was measured over a period of 28 days. The growth kinetics of mutants 88, 160 and 276 were similar to those of mutant 141. The growth kinetics of mutant 262 was similar to those of mutant 197. The growth kinetics of other first-site N-linked glycosylation mutants were similar to those of wild type virus.

Figure 6:
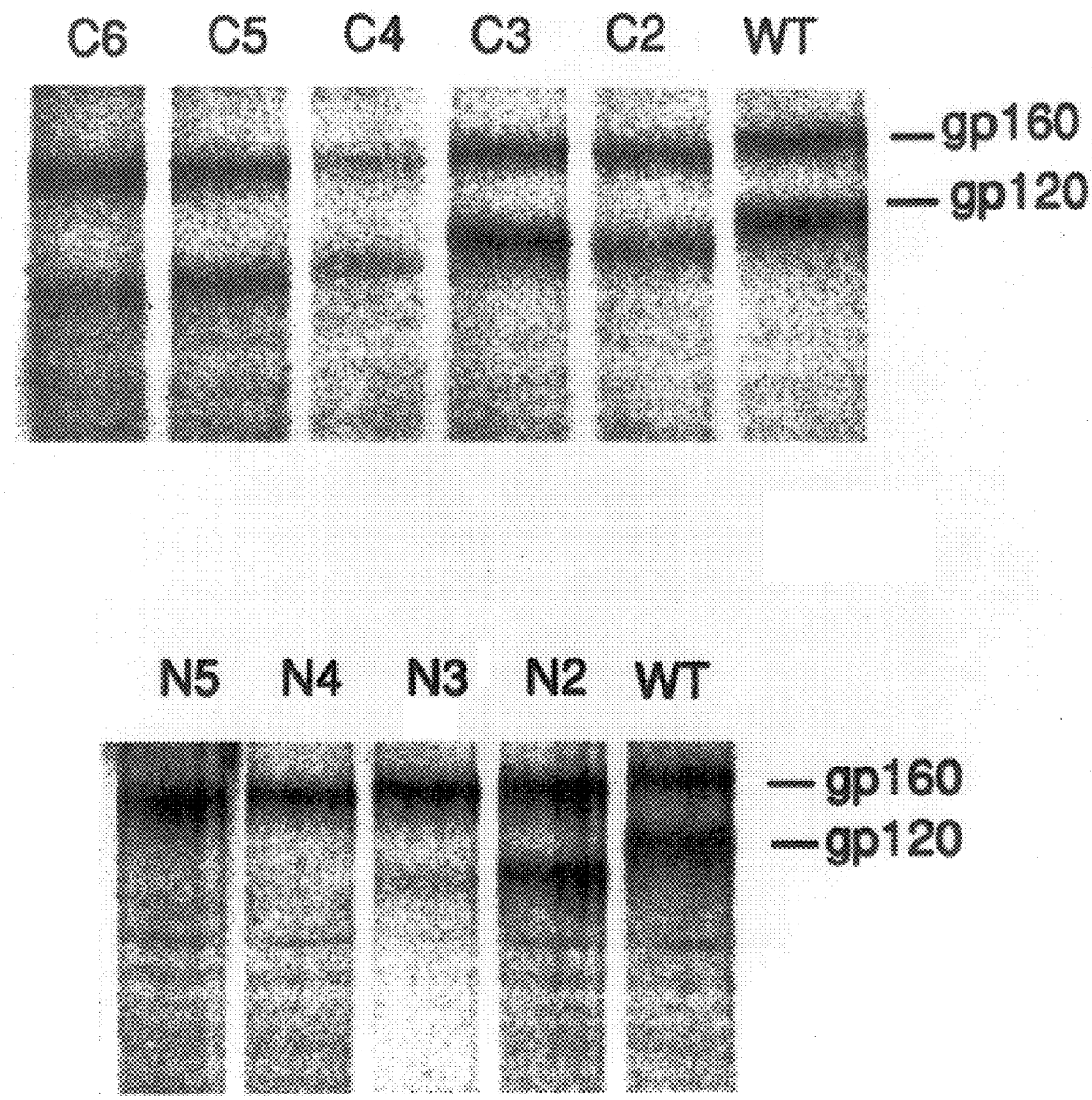

FIG. 6 is a western blot analysis of the envelope glycoproteins expressed by wild type and mutant viruses. COS-7 cell lysates were prepared 48 hours post-transfection and electrophoresed on 12% SDS-PAGE, transferred to nitrocellulose, and reacted with sheep anti-gp120 antisera. (A) Mock, wild type and C2, C3, C4, C5 and C6 mutants. (B) Mock, wild type, N2, N3, N4 and N5 mutants.

Figure 7A:
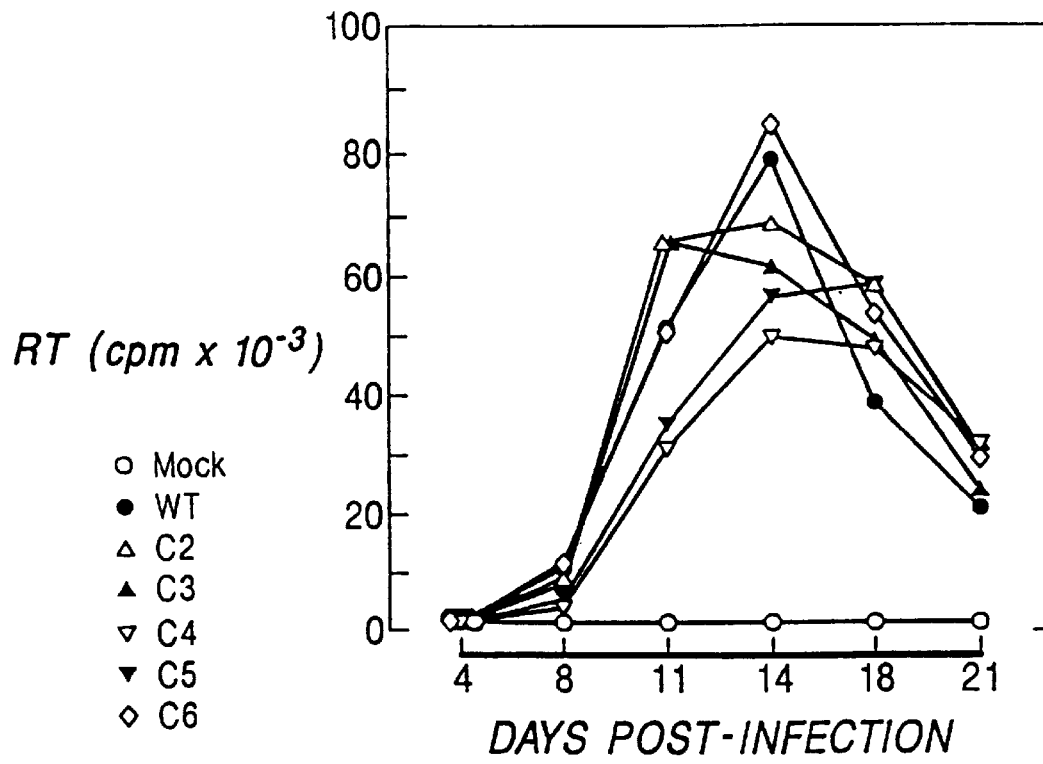

FIGS. 7A and B are graphical demonstrations of RT activity in SupT1 cells infected with wild type and mutant viruses. (A) Mock, wild type and C2, C3, C4, C5 and C6 mutants. (B) Mock, wild type and N2, N3, N4 and N5 mutants.

GENERATION OF MOLECULES USEFUL AS VACCINE CANDIDATES FOR HIV-1

As outlined above, proteins according to the invention are recombinant human immunodeficiency virus envelope glycoproteins which are mutated with respect to a wild type (native) human immunodeficiency virus glycoprotein in the primary amino acid sequence to effect partial deglycosylation. The genetic change should be introduced to positions in the C-terminal portion of gp120 (between the C-terminus of gp120 and a specific cysteine which forms the loop containing V3). Notwithstanding the mutation(s), the conformation of the glycoprotein remains sufficiently intact to maintain infectivity when present as a component of the virion. We propose that, in individuals that are immunized with this molecule, an immune response will be induced to reduce or block viral infectivity.

As illustrated by the studies described below, potential N-linked glycosylation sites in gp120 can be systematically mutated, either singly or in combination by site directed mutagenesis such that the consensus glycosylation sequence is disrupted. Recombinant viruses are generated containing gp120 genes that have such mutations. To determine whether the conformation is retained in the mutated gp120, the infectivity of each mutant virus is measured. Processing of gp160 to gp120 and gp41 may also be assessed as a rough measure of retention of conformation and infectivity.

In general there are more than 20 consensus N-linked glycosylation sites in the gp120 coding sequence of HIV-1 isolates. For illustrative purposes, we have shown the positions of these sites on gp120 in HXB2 and in other strains of HIV-1 in FIG. 1. The relative positions of these sites on the predicted structure of gp120 in HXB2 are shown in FIG. 2. A linear map of the conserved N-linked glycosylation sites, their relative positions and their level of conservation are presented in FIG. 3.

In FIG. 3, the following residue designations correspond to the arrows of gp120:

| | | |
|---|---|---|
| a1 = 88 | a5 = 241 | a9 = 356 |
| a2 = 136 | a6 = 262 | b9 = 386 |
| b1 = 141 | a7 = 276 | b11 = 392 |
| a3 = 156 | b5 = 289 | b12 = 397 |
| b2 = 160 | a8 = 295 | b13 = 406 |
| a4 = 186 | b6 = 301 | a10 = 448 |
| b3 = 197 | b7 = 332 | a11 = 463 |
| 230 not marked | b8 = 339 | |
| b4 = 234 | | |

Sequence information for envelope proteins of other strains (e.g. the strains listed above) are referenced in Myers et al. Human Retroviruses and AIDS (1991): "A compilation and analysis for nucleic acid and amino acid sequences" (Los Alamos National Laboratory, Los Alamos, N. Mex.), which is hereby incorporated by reference.

The following studies are provided to illustrate (not to limit) the invention, and particularly to illustrate methods for readily determining the relative importance of each of the various HIV envelope N-linked glycosylation sites and the effect of mutations to those sites and combinations thereof.

Mutation of Potential N-Linked Glycosylation Sites and the Effect of these Mutations on Envelope Glycoprotein Viral Infectivity The molecular clone HXB2, which contains 24 N-linked glycosylation sites was used as the template DNA for site-directed mutagenesis as follows.

Construction of Mutants

Oligonucleotide-directed mutagenesis was performed on a 2.7 Kb SalI-BamHI fragment of HXB2 (Cohen et al., 1990, J. AIDS 13:11), which covers all 24 N-linked glycosylation sites of gp120, using the method of Kunkel (Cohen et al., 1988, Nature 334:532). The oligonucleotide primers used for mutagenesis were synthesized using standard cyanoethyl phosphoamidite chemistry and are listed in Table I. Mutants were identified by the Sanger chain-termination method (Cullen, 1986, Cell 46:973). The SalI-BamHI fragment containing the desired mutation was excised from the replicative form of each mutant and used to replace the 2.7 Kb SalI-BamHI fragment of HXB2. All HXB2-derived N-linked glycosylation site mutants containing the designated changes were further verified by DNA sequencing (Cullen, 1986, Cell 46:973).

Western Blot Analysis of Envelope Proteins

Ten micrograms of wild type or mutant DNA was transfected into 3–5×10$^6$ COS-1 cells using DEAE-dextran (Curran et al., 1988, Science 239:610). Cells lysates were collected 48 hours after transfection. Mock-transfected, wild type, and mutant transfected COS-1 cells were washed with phosphate-buffered saline (PBS) once and subjected to centrifugation at 2500 rpms. Cell pellets were resuspended with 100 ml RIPA lysis buffer (0.15 M NaCl/0.05 M Tris HCl pH 7.2, 1% Triton X-100, 1% Sodium deoxycholate, 0.1% SDS) and spun down at 35,000 rpm (Ti70 rotor; Beckman) at 4° C. for 40 minutes. Ten microliters of cell lysates were electrophoresed in 12% SDS-polyacrylamide gels. A reference HIV-1 positive serum at a 1:200 dilution and a sheep anti-gp120 (AIDS Research Reference Reagent Program #288) at 1:2000 dilution were used for western blots as described (Dalgleish et al., 1984, Nature 312:763).

Monitoring of Syncytium-formation and Viral Infectivity

The CD4 positive human T lymphoid cell line, SupT1, was grown and maintained at 37° C. in RPMI-1640 containing 10% heat-inactivated fetal bovine serum and 1% penicillin-streptomycin. COS-1 cells were propagated in Dulbecco's minimal eagle medium supplemented with 10% heat-inactivated fetal bovine serum and 1% penicillin-streptomycin. Cell-free supernatants were collected 48 hours after transfection. Supernatants were filtered through 0.45 mm filters and assayed for virion-associated reverse transcriptase (RT) activity. Equal amounts of wild type and mutant virus, as measured by RT activity (100K cpm), was used to infect 1×10$^6$ SupT1 cells. One milliliter of the culture medium was collected every three or four days and assayed for RT. Cultures were monitored for 28 days.

Reverse Transcriptase Assay

One milliliter of culture medium was mixed with 0.5 ml 30% PEG and 0.4M NaCl on ice for 2 hours and spun at 2500 rpm at 4° C. for 30 minutes. The pellet was resuspended in 100 ml of RT buffer (0.5% Triton X-100, 15 mM Tris pH 7.4, 3 mM dithiothreitol, 500 mM KCL, 30% glycerol). Ten microliters of the solution was incubated with 90 ml of RT cocktail (40 mM Tris HCL, pH 7.8, 10 mM $MgCl_2$, 8 mM dithiothreitol, 94 ml $ddH_2O$, 0.4 U Poly (rA) oligo (dT) [optical density at 260 nm] per ml and 2.5 mCi/ml $^3$H-labeled dTTP) at 37° C. for 1.5 hours. The reaction mixture was precipitated with 3 ml of 10% trichloroacetic acid (TCA) and 10 ml of 1% tRNA which served as the carrier, and was then chilled on ice for 20 minutes. The reaction mixture was filtered through Whatman GF/C glass microfiber filters and washed 3 times with 5% TCA to remove unincorporated $^3$H-dTTP. Radioactivity was measured in a liquid scintillation counter.

Single Mutants in gp120

The ability of HXB2-derived mutants (each having one of the 24 N-linked glycosylation sites mutated by site-directed mutagenesis) to infect CD4-positive SupT1 cells was compared with that of the wild type virus and the results are described below. Most of the individual consensus N-linked glycosylation sites are dispensable for viral infectivity. N-linked glycosylation sites that are likely to play important roles in HIV-1 infectivity are not randomly distributed in gp120; they are generally located in the N-terminal half of gp120.

Since deglycosylation of proteins can improve their immunogenicity, a candidate vaccine for HIV-1 might be a partially glycosylated gp120 with most of the dispensable N-linked glycosylation sites removed, such that the conformation of the protein is largely unaltered and the CD4 binding site is retained.

Each of the 24 potential N-linked glycosylation sites in the gp120 coding region of the infectious molecular clone HXB2, was individually modified to generate 24 N-linked glycosylation site mutants (Table 1). In these mutants, the Asn-X-Ser/Thr attachment sequence was replaced by either Gln-X-Ser/Thr or His-X-Ser/Thr. The underlying hypothesis was that if a given N-linked glycosylation site played no significant role in syncytium-formation or viral infectivity, then such a mutant should retain its infectivity and its ability to form syncytia. Each of the 24 mutants was designated by the residue number of the respective N-linked glycosylation site (Table 1).

Expression of Envelope Proteins

To determine if mutations introduced to any of the 24 N-linked glycosylation sites affected the expression of the envelope protein, 10 μg each of mutant or wild type proviral DNA was transfected into 3–5×10$^6$ COS-1 cells using DEAE-dextran as described above. Cell lysates derived from COS-1 transfectants were then examined in western blots as described above. As shown in FIG. 4, Both gp160 and gp120 were detected in all 24 mutants, suggesting that no particular individual N-linked glycosylation site was indispensable for the expression of the envelope protein.

Syncytium-formation and Viral Infectivity

To evaluate whether mutations introduced into any of the individual N-linked glycosylation sites affected syncytium-formation and viral infectivity, cell-free virions obtained from the culture supernatant of COS-1 transfectants were collected at 48 hours post-transfection. Equal amounts of mutant and wild type viruses, as measured by RT activity, were used to infect CD4-positive SupT1 cells. Virus-infected cultures were monitored for syncytium formation and RT activity. As in the case of the wild type virus-infected SupT1 cultures, syncytia and RT activity were detected in all the mutant virus-infected SupT1 cultures (Table 1). However, 6 mutant viruses, mutants 88, 141, 160, 197, 262 and 276, exhibited delays in growth kinetics when compared with the wild type virus (Table 1).

Third-site N-linked Glycosylation Mutants

To examine whether the observed effect on viral infectivity in mutants 88, 141, 160, 197, 262, and 276 was due to amino acid substitutions introduced to replace the asparagine residue of the canonical N-linked glycosylation sequence with a non-canonical residue, six third-site N-linked glycosylation mutants were constructed (Table 2). These six mutants, designated 90, 143, 162, 199, 264 and 278, are called third-site mutants because they had the Ser/Thr residue of the Asn-X-Ser/Thr sequence replaced by a different amino acid residue.

The ability of these six third-site mutants to infect CD4-positive SupT1 cells was also examined. If the phenotype of a third-site N-linked glycosylation mutant is similar to that of the wild type virus, it is likely that the observed defect in infectivity for the corresponding first-site mutant is the result of amino acid substitution at the first site rather than the loss of that particular N-linked glycosylation site. For instance, mutant 162 was indeed found to have similar growth kinetics to the wild type virus (Table 2). This suggested that the impairment of viral infectivity observed for mutant 160 in SupT1 cells was likely due to the substitution of asparagine residue with a glutamine residue at this particular consensus N-linked glycosylation site; but not due to the loss of this particular consensus N-linked glycosylation site. The remaining five third-site N-linked glycosylation mutants, like their respective first-site mutants, all showed partial impairment in infectivity when compared with the wild type virus (Table 2).

Mutations Introduced at Combinations of N-Linked Glycosylation Sites

Additional mutants in potential N-linked glycosylation sites in gp120 were generated by oligodeoxynucleotide directed mutagenesis as described above. The 2.7 Kb SalI-BamHI fragment of the molecular provirus clone HXB2, was cloned into bacteriophage M13mp18 at SalI-BamHI sites and was used as the template for mutagenesis. The oligonucleotides used for the mutagenesis are listed in the Table 1. Changes were made from the consensus N-linked glycosylation sequence Asn-X-Ser/Thr (N-X-S/T) to either Gln-X-Ser/Thr (Q-X-S/T) or His-X-Ser/Thr (H-X-S/T). Five mutants were generated each of which was altered at the amino acids contained within the parentheses as follows: C2, (386/486); C3(397/463); C4 (386/392/397/463); C5 (386/392/397/406/463); and C6 (386/392/397/406/448/463) (Table 3). The mutations were confirmed by Sanger sequencing (Sanger et al., 1977, Proc. Natl. Acad, Sci. USA 74:5463).

Expression of Envelope Proteins and Effect of Combinations of Mutations on Viral Infectivity Mutant proviral DNA and wild type DNA (3 μg) was transfected into 3×10$^6$ COS-7 cells (a monkey kidney cell line, CV-1, origin minus, SV40) using DEAE-dextran as described above. Cell lysates from COS-7 transfected cells collected 48 hours after transfection were examined by western blotting. Proteins were separated by SDS-polyacrylamide gel electrophoresis, transferred to nitrocellulose, and reacted with sheep anti-gp120 antisera (Chou et al., 1988, J. Infect. Dis. 157:805) (FIG. 4). Wild type DNA and all of the C-terminal mutants C2, C3, C4, C5, and C6 expressed gp160 and gp120 proteins at ratios similar to each other demonstrating that the position of the mutations has no apparent effect on cleavage of gp160 to gp120 and gp41. However, the mobilities of the mutated proteins is higher (faster) than those of the wild type (FIG. 6, Top) suggesting that some carbohydrates have been removed from these mutant proteins. In conclusion, oligosaccharides at the C-terminal region of gp120 appear to be dispensable for cleavage of gp160 to gp120/gp41.

To test the effect of the removal of carbohydrates from the C-terminal region of gp120 on viral infectivity, cell free virus obtained from these mutants was used to infect the CD4-positive T cell line, SupT1. Supernatants were collected from COS-7 transfected cells 48 hours post-transfection. RT assays were performed and were used as a measure of the amount of virus in the supernatant. An equal amount of virus, adjusted to an RT activity of approximately 400K cpm, was used to infect 4×10$^6$ SupT1 cells. The infectivity of wild type and mutant viruses was determined by examining the cultures for the formation of syncytia and by measuring RT activity as described above. Syncytia were apparent in cultures infected with each of the mutants beginning at day 4 postinfection and the formation of syncytia progressed with similar kinetics in each culture (FIG. 7A). Thus, the carbohydrates at C-terminal of gp120, which encompass the CD4-binding region, are not essential for viral infectivity.

Figure 7B:
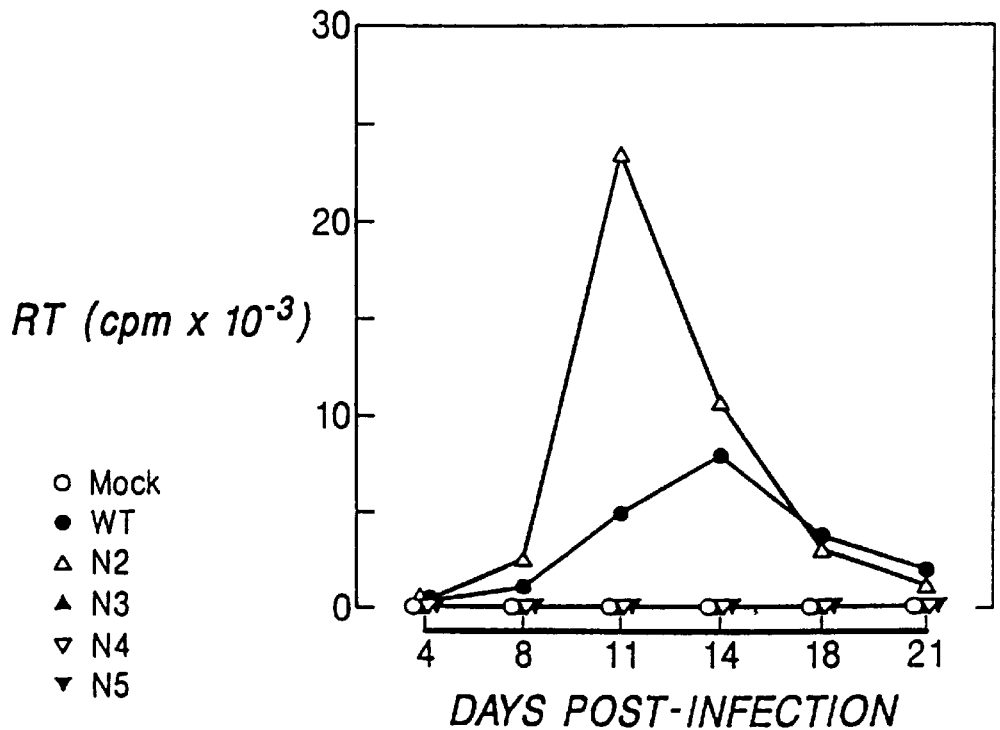

To determine whether other regions of gp120 could be deglycosylated without affecting processing of gp160 and infectivity, another heavily glycosylated region located at the N-terminus of gp120, from cysteine 126 to cysteine 196, was mutated. The oligonucleotides used for mutagenesis are summarized in Table 1. Four N-terminal mutants, N2(141/186), N3 (141/160/186), N4 (136/141/160/186), and N5 (136/141/156/160/186) were generated (Table 3). Mutants N3, N4 and N5 were defective in processing of gp160. Cultures infected with mutant N2, which had two mutated N-linked glycosylation sites formed syncytium at day 4 post-infection and had a higher RT activity than that of the wild type (FIG. 7B). In contrast, removal of more than three N-linked glycosylation sites (mutants N3, N4, and N5) in the N-terminal region of gp120 significantly reduced viral infectivity, in that no syncytia could be observed at any time postinfection.

The data described above demonstrate that six N-linked glycosylation sites at the C-terminal of gp120 spanning the CD4-binding region are not essential for processing of gp160 or for viral infectivity. Binding of gp120 to CD4 is essential for infection of CD4-positive T cells. The data described above suggest that carbohydrates that cover the CD4 binding region are not important for the gp120/CD4 interaction. However, carbohydrates at the N-terminal Cys 126–196 loop of gp120 are important for envelope processing and for viral infectivity. For vaccine production, the N-linked glycosylation sites in the cys 126–196 loop containing the V1 and V2 sequences preferably are to be maintained to provide optimum proper conformation of the gp120 molecule.

More Detailed Analysis of the Effect of Combinations of Mutants on Viral Infectivity and Envelope Processing Using the methods described above, additional combinations of mutations were introduced into the C-terminal portion of the gp120 of HIV-1 in the molecular clone HXB2, to study the effect of these mutations on viral infectivity. The results are presented in Table 4. The amino acid numbers of the first amino acid in each consensus sequence are listed along the top of the table. Mutations in any given site are indicated by a "−" symbol, whereas wild type consensus N-linked glycosylation sites are indicated by a "+" symbol. It is clear from the data in the table that some combinations of mutations result in loss of, or impaired infectivity, while others have no effect. For example, in row S seven N-linked glycosylation sites have been mutated without affecting viral infectivity and in row W a combination of eight mutations have been introduced that do not affect infectivity. In contrast, the particular combination of seven mutations (shown in rows Q and T) result in impaired infectivity and additional combinations of nine and ten (see row U and V, respectively) significantly reduce or eliminate viral infectivity. It is also evident from the data that the N-linked glycosylation site at amino acid number 289 plays a role in infectivity when other N-linked glycosylation sites in the C-terminal portion of the molecule are also mutated. Thus, it is preferable for the mutant protein to have a wild type residue at position 289 if the molecule contains additional C-terminal mutations.

Generation of Partially Deglycosylated gp120 for Use as a Candidate Vaccine

Candidate vaccine gp120 molecules should generally possess the following properties: 1) they should be partially deglycosylated in the C-terminal portion of the molecule (defined above) to a sufficient extent to permit immune recognition of this portion of the molecule; and 2) a sufficient amount of the wild type conformation of the molecule should be retained such that the mutant virus substantially retains infectivity. A recombinant gp120 molecule which satisfies both of these criteria is likely to elicit a protective immune response to reduce viral infectivity.

Recombinant gp120 molecules derived from any strain of HIV-1 which satisfy the criteria listed above can be generated using the methods described above. All that is required is a knowledge of the sequence of the gp160/gp120 gene in the particular strain of HIV-1 of interest, which if not already available, can be obtained by a skilled artisan using ordinary cloning and sequencing technology such as that described in the Molecular Cloning Manual (Sambrook et al., 1989, Molecular Cloning: A Laboratory Manual, Cold Spring Harbor Laboratory, NY). Potential N-linked glycosylation sites can be identified by locating the consensus Asp-X-Ser/Thr regions and mutations and combinations thereof can be introduced into these sites as described above. Mutated molecules, wherein the mutations have substantially no effect on either infectivity, can then be identified as described above. Such molecules can be obtained by the skilled artisan without undue experimentation because the techniques and tests to be used are common and familiar to those knowledgeable in the art.

In a similar manner to that described above, gp160 molecules can be generated which are partially glycosylated in the C-terminal portion of gp120. The methods for generating such molecules are identical to those described for gp120. Partially deglycosylated gp160 can also be used as a vaccine candidate provided the C-terminal end of the gp120 portion is deglycosylated as described.

To determine whether the molecule is sufficiently deglycosylated, its mobility on a gel be compared to wild type as described above. As indicated the mutation should produce a gp120 entity of less than 90% of the wild-type molecular weight. Alternatively, chemical techniques for quantitating sugar content are well known. See, e.g., Chapin et al. IRL Press (1986) pp. 178–181 and Methods of Carbohydrate Chemistry Vol. 7 (Whistler et al. Eds.) Academic Press (1976) p. 198 which describe acid hydrolysis and methanolysis. After methanolic hydrolysis, monosaccharides are derivatized e.g., to trimethysilyl ethers of the methyl glycosides. Quantitation is accomplished by gas chromatography using parallel external standards of monosaccharide mixtures. Alternatively total sugar content of a glycoprotein of known amino acid sequence can be determined by mass spectroscopy to obtain accurate mass of glycosylated and unglycosylated moieties.

Expression of Recombinant Partially Deglycosylated gp120

Large quantities of recombinant partially deglycosylated gp120 or gp160 mutant glycoproteins can be obtained by expressing these proteins in a number of expression systems. For example, chinese hamster ovary (CHO) cells can be transfected with a plasmid encoding a mutated gp120 or gp160 gene, using any number of transfection methods all of which are described in detail in Sambrook et al. (Supra). Mutated proteins can be expressed in a constitutive manner under the control of its own promoter under the control of another promoter such as another retrovirus LTR. Alternatively, mutated proteins can be expressed in an inducible manner, wherein expression is driven by a promoter that responds to the addition of an inducer molecule to the transfected cells. Examples of such promoters can be found in Sambrook et al. (Supra). Glycoproteins that are so expressed can be recovered from the cells and from the cell medium using common biochemical techniques. See Lasky et al. *Science* 233:209–212 (1986); Robey et al. *Proc. Nat'l. Acad. Sci.* 83:7023–7027 (1986); Pyle et al. *Aids Research and Human Retrovirus* 3:387–399 (1987).

A baculovirus expression system can also be used to obtain large quantities of partially glycosylated gp120 or gp160. A gene encoding a mutated glycoprotein can be cloned into a commercially available baculovirus transfer plasmid. A recombinant baculovirus encoding such a protein can be generated as described by Summers and Smith (1988, A Manual of Methods for Baculovirus Vectors and Insect Cell Culture Procedures: Texas Agricultural Experiment Station Bulletin No. 1555, College Station, Tex.). The virus can be used to infect insect cells, such as Sf9 cells, whereupon the mutated glycoprotein will be expressed to high levels as the baculovirus replicates. Protein is recovered from the culture using ordinary standard biochemical techniques.

The mutated proteins can also be produced as part of a viral particle, with or without alterations to other portions of the virus. See, e.g. the method of Aldovini et al. *J. Virol.* 64:1920–1926 (1990).

Generation of Antibodies

Recombinant envelope proteins can be used to generate antibodies using standard techniques, well known to those in the field. For example, the proteins are administered to challenge a mammal such as a goat, rabbit or mouse. The resulting antibodies can be collected as polyclonal sera, or antibody-producing cells from the challenged animal can be immortalized (e.g. by fusion with an immortalizing fusion partner) to produce monoclonal antibodies. Monoclonal antibody-producing hybridomas (or polyclonal sera) can be screened for antibody binding to the protein and to wild type envelope. They can also be screened for the ability to neutralize infectivity of HIV-1 isolates, preferably multiple (e.g., at least 3) isolates each having diverse sequences in the hypervariable V3 region. By antibodies we include constructions using the binding (variable) region of such antibodies, and other antibody modifications.

Vaccines

The mutant envelope protein may be formulated into vaccines according to standard procedures known to those in the field. For example, procedures currently used to make wild-type envelope protein vaccines (e.g., Microgenysys gp160 vaccine) can be used to make vaccines with the selectively deglycosylated envelope protein. Various modifications such as adjuvants and other viral or toxin components known for such vaccines or immunotherapeutics may be incorporated with the mutants.

TABLE 1

N-linked Glycosylation Mutants of HXB2 Envelope Glycoprotein

| MUTANT VIRUS | AMINO ACID CHANGE | MUTAGENIC OLIGONUCLEOTIDE(5' to 3')* | | VIRAL INFECTIVITY |
|---|---|---|---|---|
| 88  | Asn to Gln | TAGTATTGGTACAGGTGACAGAAAATTT | (SEQ ID NO:1)  | +** |
| 136 | Asn to Gln | TGATTTGAAGCAGGATACTAATAC      | (SEQ ID NO:2)  | +   |
| 141 | Asn to Gln | ATACTAATACCCAAAGTAGTAGCGGGA   | (SEQ ID NO:3)  | +** |
| 156 | Asn to Gln | GATAAACAGTGCTCTTTCAATAT       | (SEQ ID NO:4)  | +   |
| 160 | Asn to Gln | CTGCTCTTTCCAGATCAGCACAAG      | (SEQ ID NO:5)  | +** |
| 186 | Asn to Gln | TACCAATAGATCAGGATACTACCAGC    | (SEQ ID NO:6)  | +   |
| 197 | Asn to Gln | TGACAAGTTGTCAGACCTCAGTCAT     | (SEQ ID NO:7)  | +** |
| 230 | Asn to His | TAAAATGTAATCATAAGACGTTCA      | (SEQ ID NO:8)  | +   |
| 234 | Asn to His | ATAAGACGTTCCATGGAACAGGACCA    | (SEQ ID NO:9)  | +   |
| 241 | Asn to Gln | GACCATGTACACAGGTCAGCACAGTAC   | (SEQ ID NO:10) | +   |
| 262 | Asn to Gln | ACTGCTGTTACAAGGCAGTCTAG       | (SEQ ID NO:11) | +** |
| 276 | Asn to Gln | TTAGATCTGTCCAGTTCACGGACAAT    | (SEQ ID NO:12) | +** |
| 289 | Asn to Gln | TAGTACAGCTGCAGACATCTGTAGAAA   | (SEQ ID NO:13) | +   |
| 295 | Asn to Gln | CTGTAGAAATTCAATGTACAAGAC      | (SEQ ID NO:14) | +   |
| 301 | Asn to His | ACAAGACCCAACCACAATACAAGAAA    | (SEQ ID NO:15) | +   |
| 332 | Asn to His | GCACATTGTCACATTAGTAGAGC       | (SEQ ID NO:16) | +   |
| 339 | Asn to Gln | GCAAAATGGCAGAACACTTTAAAAC     | (SEQ ID NO:17) | +   |
| 356 | Asn to Gln | ATTCGGAAATCAGAAAACAATAATCTTTA | (SEQ ID NO:18) | +   |
| 386 | Asn to Gln | TTTCTACTGTCAGTCAACACAACTG     | (SEQ ID NO:19) | +   |
| 392 | Asn to Gln | ACAACTGTTTCAGAGTACTTGGTTTAATAG| (SEQ ID NO:20) | +   |
| 397 | Asn to Gln | GTACTTGGTTTCAGAGTACTTGGAG     | (SEQ ID NO:21) | +   |
| 406 | Asn to His | CTGAAGGGTCACATAACACTGAAGGA    | (SEQ ID NO:22) | +   |
| 448 | Asn to Gln | GATGTTCATCACAGATTACAGGGCTG    | (SEQ ID NO:23) | +   |
| 463 | Asn to His | GGTAATAGCAACCATGAGTCCGAGAT    | (SEQ ID NO:24) | +   |

* Underlined type indicates mutation sites,
**Partial impairment

TABLE 2

Third-site N-linked Glycosylation Mutants of HXB2 Envelope Glycoprotein

| MUTANT VIRUS | AMINO ACID CHANGE | MUTAGENIC OLIGONUCLEOTIDE(5' to 3')* | | VIRAL INFECTIVITY |
|---|---|---|---|---|
| 90  | Thr to Val | GGTAAATGTGGTCGACAACTTTTGACATGT | (SEQ ID NO:25) | +** |
| 143 | Ser to Ala | AATACCAATAGTGCATGCGGGAGAATGG   | (SEQ ID NO:26) | +** |
| 162 | Ser to Ala | CTGCTCTTTCAATATTGCCACAAGCATAAG | (SEQ ID NO:27) | +   |
| 199 | Thr to Glu | GTTGTAACACCGAAGTCATTACACAG     | (SEQ ID NO:28) | +** |
| 264 | Ser to Ala | CTGCTGTTAAATGGCGCTCTAGCAGAAGAAGAG | (SEQ ID NO:29) | +** |
| 278 | Thr to Val | CTGTCAATTTCGTCGTCGACAATGCTAAA  | (SEQ ID NO:30) | +** |

* Underlined type indicates mutation sites
** Partial impairment

TABLE 3

Combination N-linked glycosylation sites mutants of HXB2 env glycoprotei

| Mutant | amino acid change | gp160 cleavage | viral infectivity |
|---|---|---|---|
| C2 | 386/463 | + | + |
| C3 | 397/463 | + | + |
| C4 | 386/397/406/463 | + | + |
| C5 | 386/392/397/406/463 | + | + |
| C6 | 386/392/397/406/448/463 | + | + |
| N2 | 141/186 | + | + |
| N3 | 141/160/186 | +* | − |
| N4 | 141/156/160/186 | − | − |
| N5 | 141/136/156/160/186 | − | − |

+*: severe impairment

TABLE 4

Additional combinations of N-Linked Glycosylation Mutants in the C-Terminal Portion of gp120

| | N-Linked Glycosylation Site Amino Acid Number | | | | | | | | | | | | | Viral |
|---|---|---|---|---|---|---|---|---|---|---|---|---|---|---|
| Row # | 230 | 234 | 289 | 301 | 332 | 339 | 356 | 386 | 392 | 397 | 406 | 448 | 463 | Infectivity |
| Q | + | + | + | + | − | − | − | − | + | − | − | + | − | + |
| R | + | + | + | + | − | − | + | − | + | − | − | + | − | ++ |
| S | + | + | + | − | − | − | + | − | + | − | − | + | − | ++ |
| T | + | + | − | + | − | − | + | − | + | − | − | + | − | + |
| U | − | − | − | + | − | − | + | − | + | − | − | + | − | − |
| V | − | − | − | − | − | − | + | − | + | − | − | + | − | − |
| W | − | − | + | + | − | − | + | − | + | − | − | + | − | ++ |

What is claimed is:

1. A composition comprising a mutant recombinant human immunodeficiency virus type 1 (HIV-1) envelope glycoprotein which is mutated in its primary amino acid sequence with respect to a wild type HIV-1 envelope glycoprotein, said mutant glycoprotein including two or more N-linked carbohydrate consensus amino acid sequence mutations so as to effect partial deglycosylation, said mutation being positioned between the C terminus of gp120 and the Cys at the N-terminal side of the gp120 cysteine loop containing the third hypervariable sequence (V3), said Cys being approximately at amino acid position 296, said mutant glycoprotein being sufficiently deglycosylated such that the total molecular mass of the mutant gp120 component is less than 75% of the corresponding fully glycosylated wild type gp120 component, said mutant glycoprotein being effective, when present as a component of a complete HIV virion, to enable viral infectivity.

2. The mutant glycoprotein composition of claim 1, wherein said virus is human immunodeficiency virus type 1, strain selected from the group consisting of MN, HXB2, IIIB, LAI, NL43, MFA, BRVA, SC, JH3, ALAI, BALI, JRCSF, OYI, SF2, NY5CG, SF162, JFL, CDC4, SF33, AN, ADA, WMJ2, RF, ELI, Z2Z6, NDK, JY1, MAL, U455, and Z321.

3. The mutant glycoprotein composition of claim 1, wherein said glycoprotein is gp160.

4. The mutant glycoprotein composition of claim 1, wherein said glycoprotein is gp120.

5. The mutant glycoprotein composition of claim 1, wherein said primary amino acid sequence is mutated such that one or more consensus N-linked glycosylation sequence mutation is a substitution of Asn, Ser, or Thr with a different amino acid.

6. The mutant glycoprotein composition of claim 1 wherein there are deglycosylations at multiple N-linked glycosylation attachment sites in the region between the C terminus of gp120 and the Cys on the N-terminal side of the cysteine loop containing hypervariable region 4 (V4).

7. The mutant glycoprotein composition of claim 1 in which at least one of the N-linked glycosylation sequences corresponding to positions 289 and 356 are not mutated.

8. The mutant glycoprotein of claim 1 in which at least one of the N-linked glycosylation sequences corresponding to the following position is deglycosylated: 386, 392, 397, 406 and 463.

9. A method of producing antibodies comprising:
    (a) administering to a mammal a mutant envelope protein, said protein being mutated in its primary amino acid sequence with respect to a wild type HIV-1 envelope glycoprotein, said mutant glycoprotein including two or more N-linked carbohydrate consensus amino acid sequence mutations so as to effect partial deglycosylation, said mutations being positioned between the C terminus of gp120 and the Cys at the N-terminal side of the gp120 cysteine loop containing the third hypervariable sequence (V3), said Cys being approximately at amino acid position 296, said mutant glycoprotein being sufficiently deglycosylated such that the total molecular mass of the mutant gp120 component is less than 75% of the corresponding fully glycosylated wild type gp120 component, said mutant glycoprotein being effective, when present as a component of a complete HIV virion, to enable viral infectivity; and (b) recovering said antibodies.

10. The antibodies of claim 9 wherein said antibodies are monoclonal antibodies.

* * * * *